United States Patent [19]

Faglione

[11] Patent Number: 5,057,096
[45] Date of Patent: Oct. 15, 1991

[54] GENITAL-VULVA PAD SANITARY NAPKIN CONSTRUCTION

[76] Inventor: Frances M. Faglione, 89-04 Doran Ave., Glendale, N.Y. 11385

[21] Appl. No.: 541,651

[22] Filed: Jun. 21, 1990

[51] Int. Cl.$^5$ ............................................... A61F 13/15
[52] U.S. Cl. .................................. 604/385.1; 604/358
[58] Field of Search ....................... 604/385.1, 358, 378

[56] References Cited

U.S. PATENT DOCUMENTS

| | | | |
|---|---|---|---|
| 2,331,355 | 10/1943 | Strongson | 604/385.1 |
| 3,183,909 | 5/1965 | Roehr | 604/385.1 |
| 4,678,464 | 7/1987 | Holtman | |
| 4,685,914 | 8/1987 | Holtman | |
| 4,781,713 | 11/1988 | Welch et al. | |
| 4,820,295 | 4/1989 | Chapas et al. | |

Primary Examiner—Randall L. Green
Assistant Examiner—G. Gualtieri
Attorney, Agent, or Firm—Henderson & Sturm

[57] ABSTRACT

A genital vulva pad/sanitary napkin construction (10) including a vulva pad member (12) dimensioned to be snugly received in a woman's vulva and adapted to be operatively engaged with a conventional sanitary napkin member (14) by releasable securing means (13) wherein the vulva pad member (17) functions as the primary absorption barrier to the flow of mensa through a woman's vulva.

2 Claims, 1 Drawing Sheet

GENITAL-VULVA PAD SANITARY NAPKIN CONSTRUCTION

TECHNICAL FIELD

The present invention relates to the field of sanitary napkins in general, and in particular to a specifically contoured sanitary napkins which are confined in a woman's vulva.

BACKGROUND ART

This invention was the subject matter of Document Disclosure Program Registration No. 228,232 which was filed in the United States Patent and Trademark Office on May 30, 1989.

As can be seen by reference to the following U.S. Pat. Nos. 4,678,464; 4,685,914; 4,781,713; and 4,820,295; the prior art is replete with myriad and diverse absorbent pad constructions used for personal hygiene.

While all of the aforementioned prior art constructions are more than adequate for the basic purpose and function for which they have been specifically designed, these absorbent pads still suffer from one major deficiency; that is, with regard to leakage around the periphery of the pad and the cleanliness of the woman.

Every month a woman goes through a very delicate, yet strenuous experience during her menstrual cycle. Unfortunately, the currently available sanitary pads will periodically allow the menses to leak around the sanitary napkin because the sanitary napkin shifts while the woman is walking or laying down, leaving the woman with blood stains on her cloths and/or bed sheets which causes a great deal of embarrassment for her. This is especially more so when there is a heavy flow of the menses due to childbirth, an abnormality of the lining of the vagina, or other medial reasons As a consequence of the foregoing situation, there has existed a longstanding need among females for a sanitary napkin construction that will virtually preclude the menses from spreading beyond the vulva no less being able to leak beyond the confines of the napkin surface. The provision of such a construction is a stated objective of the present invention.

DISCLOSURE OF THE INVENTION

Briefly stated, the genital vulva pad sanitary napkin construction of the present invention comprises a sanitary napkin unit releasably and operably associated with a vulva pad unit.

The sanitary napkin unit comprises an otherwise conventional sanitary napkin member having a relatively standard elongated configuration and fabricated from a generally thick sheet of absorbent, porous material having in some instances, a waterproof layer.

The vulva pad unit comprises a generally elliptical absorbent pad member having releasable securing means which allow the vulva pad unit to be operatively attached to the sanitary napkin member until such time as the absorbent pad member must be replaced with a fresh pad member.

As will be explained in greater detail further on in the specification, the vulva pad member is dimensioned and configured to fit inside a woman's vulva between the labia minora, whereby the majority of the menses will be trapped and absorbed within the confines of the vulva by the vulva pad member and any excess will be deposited and absorbed by the sanitary napkin member.

In addition, this invention will be effective in containing the menses inside the vulva where there is less chance of being smeared on the outside of the vulva and the vulva hair; which will make the woman feel cleaner because she is cleaner.

Furthermore, the releasable securing means allows the absorbent vulva pad member to be removed and replaced as often as the woman wishes. If the menstrual flow is heavy and the sanitary napkin is stained, it also has to be replaced, or in the event that the menstrual flow is light, the user may replace the vulva pad member and simply continue to wear the sanitary napkin member until the menses ceases to flow.

The genital vulva pad/sanitary napkin construction of this invention can also be used to keep a woman clean and odor free. For example, if a woman has a vaginal discharge or a slight leakage from her bladder, she can change the absorbent pad member as often as she wants, to keep herself clean and odor free.

In addition, due to numerous deaths attributed to toxic shock syndrome, the provision of the present invention may contribute to the prevention of this disease since the absorbent vulva pads are situated outside of the vagina to collect and subsequently remove any drainage that flows through the vagina. Therefore, it will not have the opportunity to breed bacteria inside the vagina.

BRIEF DESCRIPTION OF THE DRAWINGS

These and other attributes of the invention will become more clear upon a thorough study of the following description of the best mode for carrying out the invention, particularly when reviewed in conjunction with the drawings, wherein.

BEST MODE FOR CARRYING OUT THE INVENTION

Figure 1:
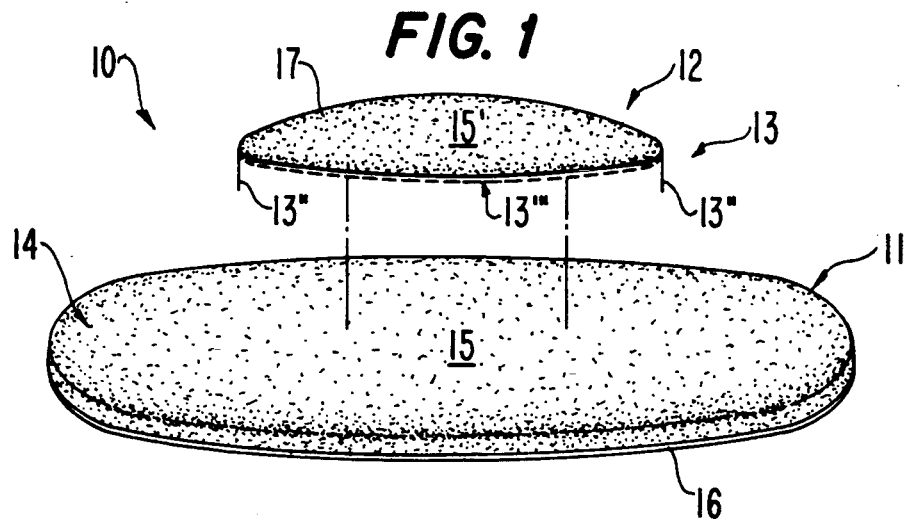
FIG. 1 is an exploded perspective view of the genital vulva pad/sanitary napkin construction that forms the basis of this invention.

As can be seen by reference to the drawings, and in particular to FIG. 1, the genital vulva pad/sanitary napkin construction that forms the basis of the present invention is designated generally by the reference numeral (10).

The construction (10) comprises in general a sanitary napkin unit (11), a vulva pad unit (12), and releasable securing means (13). These units will now be described in seriatim fashion.

As can be seen by reference to FIGS. 1 through 4, the sanitary napkin unit (11) comprises in general a conventional sanitary napkin member (14) having a generally elongated configuration and fabricated from relatively thick absorbent material (15) which is optionally provided with a moisture proof layer (16) on the bottom surface of the absorbent material (15).

As can also be appreciated by reference to FIGS. 1 through 4, the vulva pad unit (12) comprises a generally elliptical vulva pad member (17) which is also fabricated from an absorbent material (15') wherein the periphery of the vulva pad member (17) is dimensioned and configured to snugly fit a woman's vulva between the labia minora.

Figure 3:
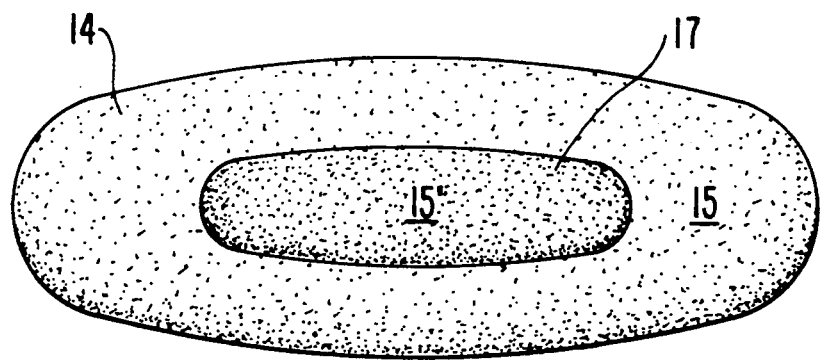
FIG. 3 is a top plan view.

Turning now to FIG. 3, it can be seen that the vulva pad member (17) is substantially shorter and narrower than the sanitary napkin member (14) whereby when the vulva pad member (17) is centrally disposed on the napkin member (14) there is a substantially absorbent surface area on the sanitary napkin member (14) which surrounds and projects beyond the outer edges of the vulva pad member (17).

Figure 2:
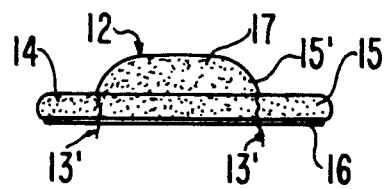
FIG. 2 is a front elevation view.
Figure 4:
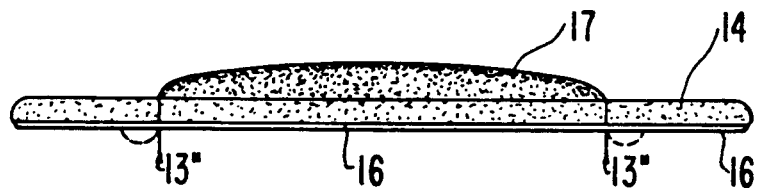
FIG. 4 is a side elevation view.

As can best be seen by reference to FIGS. 1, 2, and 4, the vulva pad member (17) is operably and releasably secured to the sanitary napkin member (14) by releasable securing means (13) which temporarily adhere the bottom of the vulva pad member (17) to the top of the sanitary napkin member (14).

The releasable securing means (13) for the purposes of this invention can comprise any suitable securing members such as threads or strings (13') or flexible tangs (13") which are capable of penetrating engagement with the absorbent material (15) of the sanitary napkin member (14), which will allow the temporary engagement and subsequent disengagement of the vulva pad member (17) relative to the sanitary napkin member (14) when it is time to remove and/or replace the vulva pad member.

Having thereby described the subject matter of the present invention, it should be apparent that many substitutions, modifications and variations of the invention are possible in light of the above teachings. It is therefore to be understood that the invention as taught and described herein is only to be limited to the extent of the breadth and scope of the appended claims.

I claim:

1. A genital vulva pad/sanitary napkin construction for absorbing mensa flow through a woman's vulva wherein the construction consists of
   a sanitary napkin unit including a sanitary napkin member fabricated from an absorbent material;
   a removable and replaceable vulva pad unit operatively associated with the sanitary napkin unit wherein the vulva pad unit comprises and elliptical vulva pad member fabricated from an absorbent material; and, wherein the vulva pad member is fabricated from an absorbent material and is dimensioned and configured to fit inside a woman's vulva; and the vulva pad member is generally centrally disposed on top of, and spaced a substantial distance from the sides of the sanitary napkin member whereby there is a substantial surface area of the absorbent material of the sanitary napkin member which surrounds the outer edges of the vulva pad member; and,
releasable securing means spaced from one another and fixedly attached on one end to the vulva pad member and having the other end penetratingly yet releasably engaged with the absorbent material of said sanitary napkin member for releasably securing the vulva pad member to the sanitary napkin member; wherein, the releasable securing means comprise flexible tangs.

2. The construction as in claim 1; wherein, the releasable securing means comprise flexible tangs.

* * * * *